United States Patent
Garzon et al.

(12) 
(10) Patent No.: US 6,277,256 B1
(45) Date of Patent: Aug. 21, 2001

(54) ENHANCED ELECTRODES FOR SOLID STATE GAS SENSORS

(75) Inventors: Fernando H. Garzon, Santa Fe; Eric L. Brosha, Los Alamos, both of NM (US)

(73) Assignee: The Regents of the University of California, CA (US)

( * ) Notice: Subject to any disclaimer, the term of this patent is extended or adjusted under 35 U.S.C. 154(b) by 0 days.

(21) Appl. No.: 09/312,803

(22) Filed: May 17, 1999

(51) Int. Cl.[7] ................................................. G01N 27/407
(52) U.S. Cl. ........................ 204/426; 204/291; 204/292; 204/424
(58) Field of Search .................................. 204/421–429, 204/291, 292

(56) References Cited

U.S. PATENT DOCUMENTS

| | | | |
|---|---|---|---|
| 3,989,614 | * 11/1976 | Tien | 204/426 |
| 4,502,939 | * 3/1985 | Holfelder et al. | 204/427 |
| 4,710,848 | 12/1987 | Schlechtriemen et al. | . |
| 4,795,533 | * 1/1989 | Young et al. | 204/421 |
| 5,366,611 | * 11/1994 | Ioannou et al. | 204/426 |
| 5,393,397 | * 2/1995 | Fukaya et al. | 204/426 |
| 5,397,025 | 3/1995 | Wachsman | . |
| 5,543,025 | 8/1996 | Garzon et al. | . |
| 5,879,525 | * 3/1999 | Kato | 204/426 |
| 6,019,881 | * 2/2000 | Kurosawa et al. | 204/426 |

OTHER PUBLICATIONS

Handbook of Chemistry and Physics, 55th ed., inside back cover, (1974–1975).*

* cited by examiner

Primary Examiner—T. Tung
(74) Attorney, Agent, or Firm—Ray G. Wilson

(57) ABSTRACT

A solid state gas sensor generates an electrical potential between an equilibrium electrode and a second electrode indicative of a gas to be sensed. A solid electrolyte substrate has the second electrode mounted on a first portion of the electrolyte substrate and a composite equilibrium electrode including conterminous transition metal oxide and Pt components mounted on a second portion of the electrolyte substrate. The composite equilibrium electrode and the second electrode are electrically connected to generate an electrical potential indicative of the gas that is being sensed. In a particular embodiment of the present invention, the second electrode is a reference electrode that is exposed to a reference oxygen gas mixture so that the electrical potential is indicative of the oxygen in a gas stream.

5 Claims, 5 Drawing Sheets

ENHANCED ELECTRODES FOR SOLID STATE GAS SENSORS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to electrochemical gas sensors, and, more particularly, to above ambient temperature solid electrolyte oxygen sensors and oxidizable gas sensors

BACKGROUND OF THE INVENTION

Solid state zirconia oxygen sensors are widely used for fuel-air stoichiometry measurements in exhaust gas streams and are ubiquitous in automotive gasoline engine control applications. These sensors also are known as lambda sensors, fuel air stoichiometry sensors or combustion control sensors. They measure the difference in potential between a platinum exhaust gas (equilibrium) electrode and a platinum air (reference) electrode to measure the thermodynamic oxygen concentration of the exhaust gas mixture. An exhaust gas contains oxidizable species such as hydrocarbons and/or carbon monoxide and oxygen gas. It has been shown that under low exhaust gas temperature conditions platinum (Pt) metal does not always catalyze automobile engine exhaust gases to equilibrium with oxygen in the exhaust stream. This results in an error in measurement in the fuel/air stoichiometry, especially under lean fuel conditions.

Oxidizable gas sensors detect oxidizable gases such as hydrocarbons, hydrogen, carbon monoxide in gas streams containing oxygen, and the like. Such sensors typically possess a nonequilibrium electrode with a very strong non-equilibrium response electrical potential and an equilibrium counter electrode that measures the equilibrium electrical potential from the gas mixture. Both of these electrodes are exposed to the analyte gas stream. A third reference electrode that is not exposed to the exhaust gas stream and that is exposed to a fixed oxygen partial pressure may also be present. This third electrode enables the simultaneous measurement of the equilibrium oxygen pressure of the gas mixture. Materials for the non-equilibrium and equilibrium electrodes for these sensors have been selected from various dissimilar materials:

1. two electrodes of dissimilar metals, e.g., platinum and gold;
2. a metal oxide mixed conductor electrode and a metal electrode, e.g., lanthanum cobalt oxide and gold;
3. two electrodes of different mixed conducting oxides, e.g., lanthanum cobalt oxide, lanthanum manganese oxide, and the like.

Sensors of the second and third type have been described previously (patent application Ser. No. 08/640,451, filed Apr. 30, 1996, Solid State Gas Sensor, incorporated herein by reference). These sensors have two electrodes with dissimilar electrocatalytic properties for the electro-oxidation of a gaseous species and the electrochemical reduction of oxygen. A mixed electrochemical potential is established on the dissimilar electrodes due to differences in electrokinetic rates for the gas-ion redox reactions. A counter electrode develops a potential that is closer in value to the Nernstian equilibrium oxygen potential for the mixture than the working electrode. The difference between the mixed potentials established on the electrodes is the sensor output signal.

Sensors for measuring oxidizable gas concentrations in exhaust gas streams should have a working electrode with a very strong nonequilibrium response and an equilibrium electrode that measures the equilibrium potential of the gas mixture. In the combustion gas application, the sensors typically run colder than zirconia oxygen sensors and effective catalysis at the equilibrium electrode is an important requirement over a working temperature range of interest.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the present invention includes a solid state gas sensor for generating an electrical potential between an equilibrium electrode and a second electrode indicative of a gas to be sensed. A solid electrolyte substrate has the second electrode mounted on a first portion of the electrolyte substrate and a composite equilibrium electrode including conterminous transition metal oxide and Pt components mounted on a second portion of the electrolyte substrate. The composite equilibrium electrode and the second electrode are electrically connected to generate an electrical potential indicative of the gas that is being sensed.

In a particular embodiment of the present invention, the second electrode is a reference electrode that is exposed to a reference oxygen gas mixture so that the electrical potential is indicative of the oxygen in a gas stream.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

In accordance with the present invention, a new class of composite electrode materials, formed as either bilayer or cermet structures, provides improved equilibrium electrodes for developing an equilibrium oxygen potential in a gas sensor, such as a lambda gas sensor or an oxidizable gas sensor. These equilibrium electrodes use conterminous platinum metal/transition metal oxide combinations, such as platinum/terbium zirconium yttrium oxide. The material combinations may be formed as a bilayer electrode or as a cermet electrode. Such material combinations have shown improved performance over either homogeneous (single phase) metal or metal oxide equilibrium (or counter) electrodes.

Figure 1:
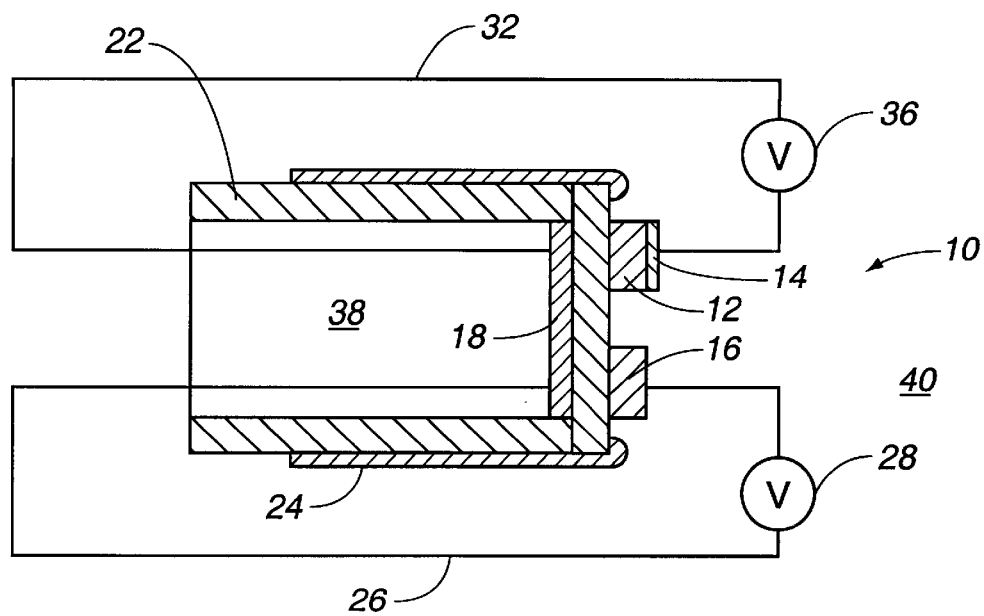
FIG. 1 is a schematic drawing of an experimental sensor assembly according to one embodiment of the present invention.

As shown in FIG. 1, an experimental cell 10 was constructed having an oxygen sensor of composite equilibrium electrode 12/14 and air reference electrode 18 and an oxidizable gas sensor of composite equilibrium electrode 12/14 and nonequilibrium electrode 16. FIG. 1 shows the oxygen sensor components and the oxidizable gas sensor components mounted on a common substrate, e.g., a zirconia substrate. It will be understood that each sensor has a separate utility and the components may be readily provided on individual electrolyte substrates according to the teachings herein.

Composite electrode 14 and reference electrode 18 were mounted on first and second portions of a zirconia solid electrolyte substrate 22 comprising opposing sides of substrate 22. Zirconia substrate 22 was formed as a tube to permit reference electrode 18 to be exposed to a reference gas 38, e.g., air, while composite electrode 12/14 was exposed to a gas stream 40 having gases to be sensed. Composite electrode 12/14 and nonequilibrium electrode 16 are mounted on first and second portions of electrolyte substrate 22 on the same side of substrate 22.

The potential generated by nonequilibrium electrode 16 was measured by voltmeter 28, which was connected to nonequilibrium electrode 16 and reference electrode 18 by circuit 26. Likewise, the potential generated by composite equilibrium electrode 12/14 was measured by voltmeter 36, which connected equilibrium electrode 12/14 to reference electrode 18 through circuit 32. Glass seal 24 isolated gas environment 40 from reference gas environment 38. In this instance, composite equilibrium electrode 12/14 is electrically connected to nonequilibrium electrode 16 through substrate 22, nonequilibrium electrode 18, and circuits 26 and 32. Then the difference in voltages measured by voltmeters 28 and 36 is indicative of the oxidizable gas in the gas stream 40.

In experimental cell 10, the potential developed by a bilayer platinum 14/terbium zirconium yttrium oxide composite equilibrium electrode (Pt/TbYSZ) 12 and the potential developed by a platinum (Pt) nonequilibrium electrode 16 were compared. In a bilayer structure, the transition metal oxide layer 12 was deposited by electron beam deposition and the Pt layer 14 was then deposited over metal oxide layer 12 by an electron beam as a solid layer generally conterminous with metal oxide layer 12. Reference Pt electrode 18 was deposited by an electron beam at the same time. Suitable thicknesses are 2500–5000 angstroms for metal oxide layer 12 and about 5000 angstroms for Pt cover layer 14. Porosity was induced in Pt layer 14 and reference Pt electrode 18 by annealing the sensor for a time and temperature to induce the desired porosity (e.g., 950° C. for 15–20 min.).

Figure 2:
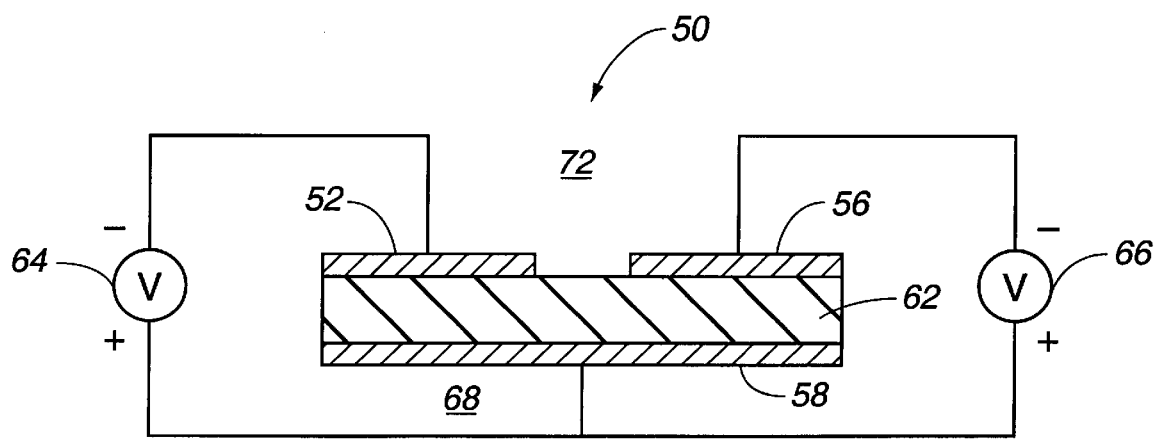
FIG. 2 is a schematic drawing of an alternate embodiment of a sensor assembly according to the present invention.

FIG. 2 schematically depicts cell 50 in an alternate embodiment to measure simultaneously the potentials of composite equilibrium electrode 52 and nonequilibrium electrode 56 with respect to a common gas reference electrode 58. Equilibrium electrode 52 and reference electrode 58 are mounted on opposite sides of a zirconia substrate 62 where reference electrode 58 is exposed to a reference gas, e.g., air, while the other electrodes 52, 56 are exposed to a gas stream having oxidizable gases. Equilibrium electrode 52 and nonequilibrium electrode 56 are mounted on first and second portions of substrate 62.

The potential generated by reference electrode 58 is measured by voltmeter 66, which is connected, to nonequilibrium electrode 56 and reference electrode 58. Likewise, the potential generated by composite equilibrium electrode 52 is measured by voltmeter 64, which is connected to nonequilibrium electrode 56. The output of voltmeter 64 is indicative of the oxygen in gas stream 72. The difference between the outputs of voltmeter 64 and voltmeter 66 is indicative of the oxidizable gas in gas stream 72.

In the embodiment shown in FIG. 2, composite equilibrium electrode 52 is formed as a cermet material of a mixture of platinum and a transition metal oxide, such as terbium zirconium yttrium oxide. The cermet or bilayer composite electrode structure may be used on either structure shown in FIGS. 1 and 2. FIGS. 1 and 2 depict a three-electrode structure for purposes of illustrating the advantages of the composite electrode structure. The composite electrode may be used in the three electrode structure or in individual oxygen sensors and oxidizable gas sensors as discussed above.

FIGS. 3–6 show the potential developed by an equilibrium electrode and a nonequilibrium electrode when the nonequilibrium electrode was exposed to low concentrations of a gas to be detected in a 1% oxygen/99% nitrogen mixture at 550° C. while the reference electrode was exposed to air as the reference gas. The square symbols represent the sensor output for a Pt electrode as the gas sensing (nonequilibrium) electrode. The upright triangles represent the sensor output data for the equilibrium electrode in the presence of a selected oxidizable gas. The calculated Nernstian thermodynamic equilibrium potential with complete oxidation of the sensed gas in the gas mixture is represented by the inverted triangles. The round symbols represent the change of potential of a device due to the dilution of oxygen in the mixture.

Figure 3:
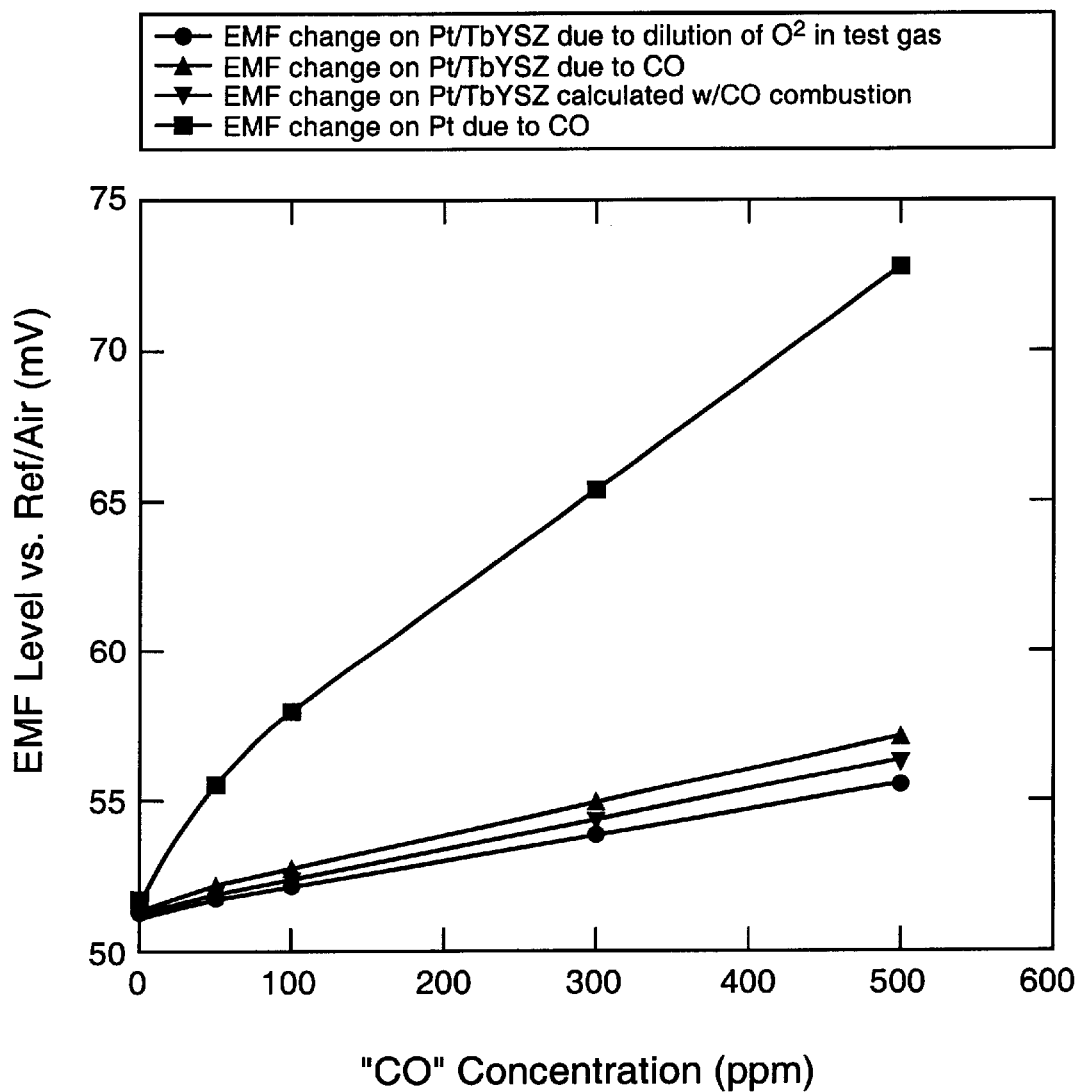
FIG. 3 graphically depicts the performance of the experimental sensor assembly for CO shown in FIG. 1 with an equilibrium electrode formed of bilayer Pt/TbYSZ.

FIG. 3 depicts the performance of a sensor having a bilayer Pt/TbYSZ electrode as the reference electrode in a sensor for measuring CO. It is clear that the Pt nonequilibrium electrode develops a potential that is far away from the calculated equilibrium potential, while the composite bilayer equilibrium electrode produces a signal very close to the theoretical Nernstian equilibrium value, which is indicative of almost complete oxidation of the sensed gas by the electrode.

Figure 4:
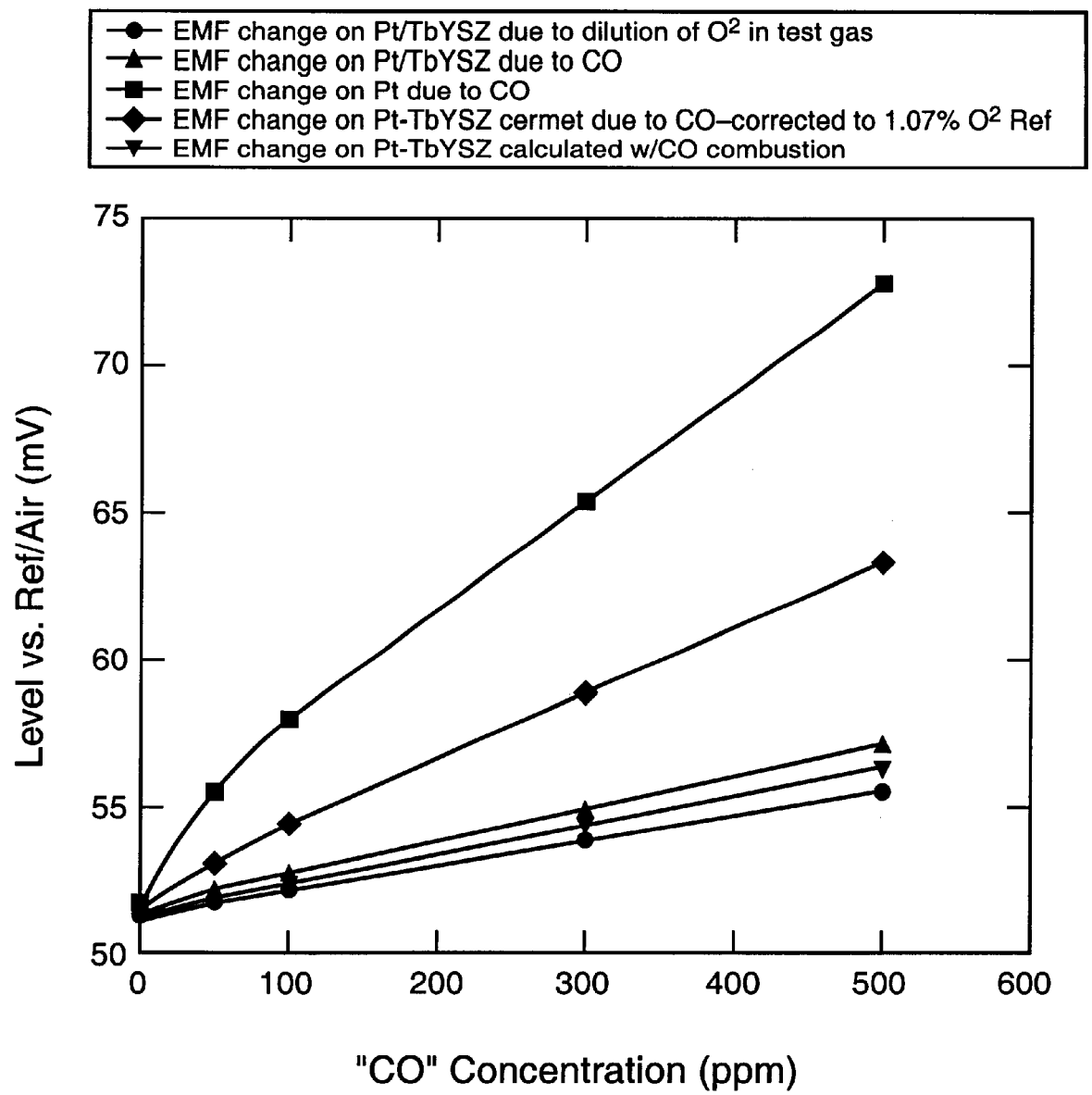
FIG. 4 graphically depicts the performance of the experimental sensor assembly for CO shown in FIG. 2 with an equilibrium electrode formed of cermet Pt—TbYSZ.

FIG. 4 depicts the performance of a sensor having a cermet Pt/TbYSZ electrode as the reference electrode in a sensor for measuring CO compared with the performance of the bilayer cell performance, also shown in FIG. 1. The cermet material was formed by co-depositing Pt and TbYSZ at 50% each by weight from two sources using two electron beam guns. The cermet material was deposited to a thickness of about 0.4 μm for the results shown in the figures. A preferred deposition range is 0.25–1.0 μm.

As seen in FIG. 4, the electrode performance was not as good as the bilayer electrode performance shown in FIG. 3, but was better than the Pt electrode performance (where the term "better" means an output that is closer to the Nernstian equilibrium values). However, neither the electrode thickness nor the composition mixture ratio was optimized for this application. A clear distinction over the Pt electrode performance is demonstrated.

Figure 5:
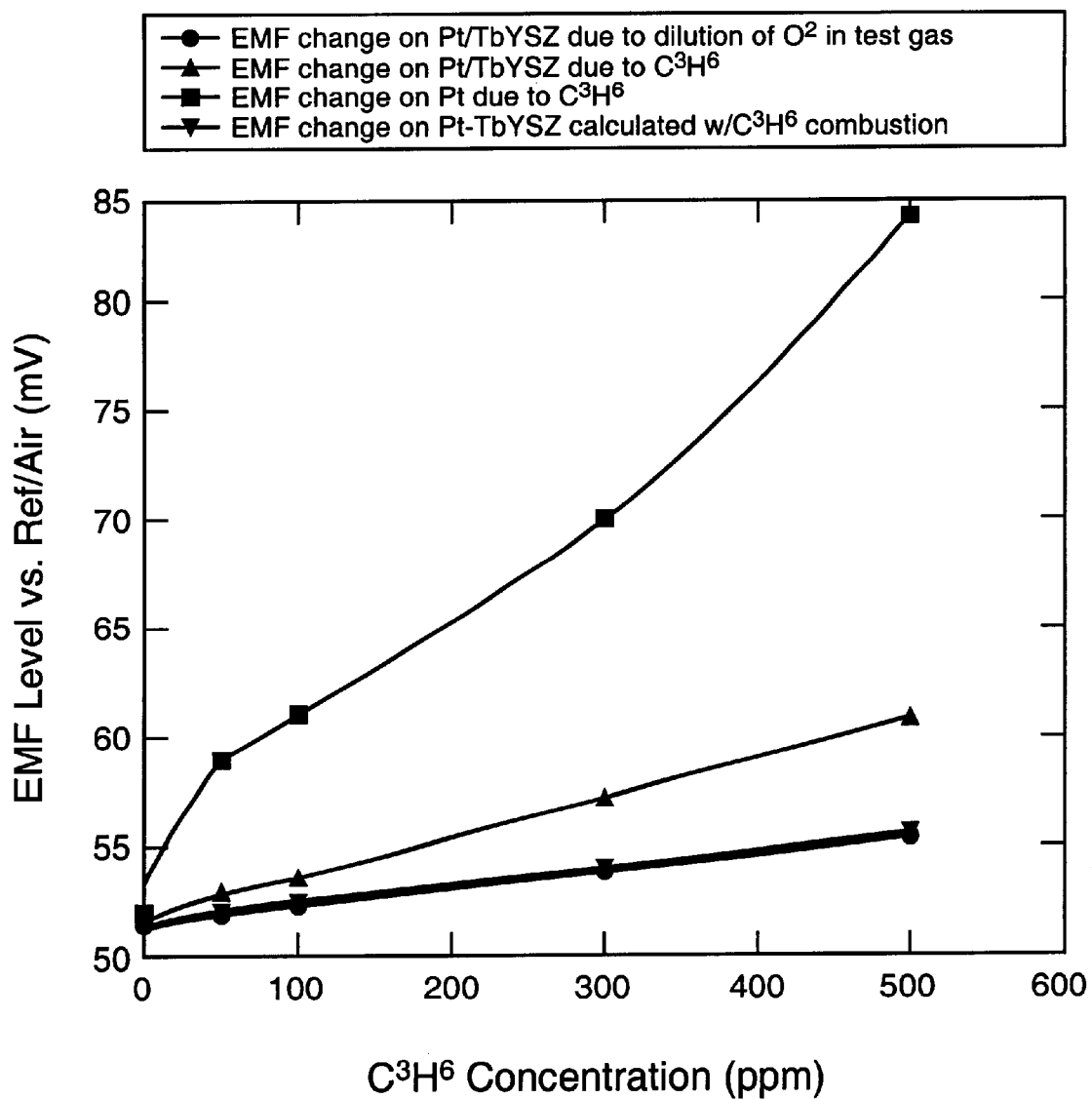
FIG. 5 graphically depicts the performance of the experimental sensor assembly for $C_3H_6$ (propylene) shown in FIG. 1 with an equilibrium electrode formed of bilayer Pt/TbYSZ.

FIG. 5 depicts the performance of a sensor having a bilayer Pt/TbYSZ electrode as the reference electrode in a sensor for measuring propylene ($C_3H_6$). Again, there is a substantial difference between the EMF generated by the Pt nonequilibrium electrode and the equilibrium electrode.

Figure 6:
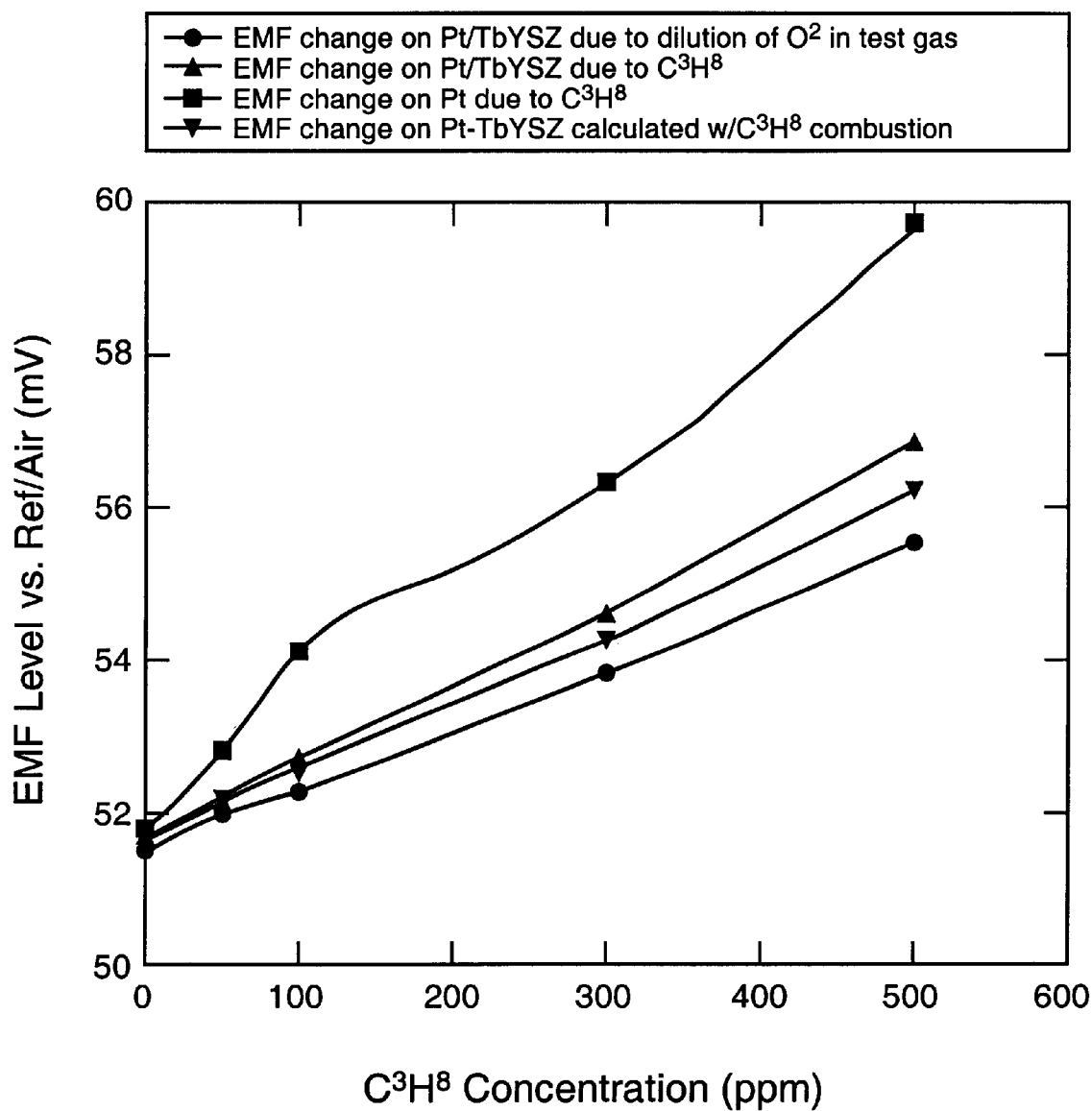
FIG. 6 graphically depicts the performance of the experimental sensor assembly for $C_3H_8$ (propane) shown in FIG. 1 with an equilibrium electrode formed of bilayer Pt/TbYSZ.

FIG. 6 depicts the performance of a sensor having a bilayer Pt/TbYSZ electrode as the equilibrium electrode in a sensor for measuring propane ($C_3H_8$). There is a substantial difference between the EMF generated by the Pt nonequilibrium electrode and the equilibrium electrode.

The enhanced electrocatalysis obtained by the equilibrium composite electrode suggested by the above response data is probably the result of lattice oxygen donated by the transition metal oxide to promote the electrooxidation at the gas-electrode interface of a gas that is to be measured. Terbium is one nonstoichiometric solid known to have the ability to release oxygen under appropriate conditions.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A solid state gas sensor for generating an electrical potential between an equilibrium electrode and a second electrode indicative of a gas to be sensed comprising:

a solid electrolyte substrate;

the second electrode mounted on a first portion of the electrolyte substrate; and a composite equilibrium electrode including conterminous terbium zirconium yttrium oxide and Pt components mounted on a second portion of the electrolyte substrate and electrically connected to the second electrode to generate an electrical potential indicative of the gas that is being sensed.

2. A solid state gas sensor according to claim 1, where the composite equilibrium electrode further comprises;

a layer of terbium zirconium yttrium oxide deposited on the second portion of the second side of the electrolyte substrate; and a Pt layer deposited on the terbium zirconium yttrium oxide layer to form a bilayer electrode structure.

3. A solid state gas sensor according to claim 1, where the composite equilibrium electrode further comprises:

a layer of terbium zirconium yttrium oxide and Pt deposited together on the second portion of the second side of the electrolyte substrate to form a mixed cermet electrode layer.

4. A solid state gas sensor according to any one of claims 1–3, where the sensor is an oxygen sensor and the composite equilibrium electrode and second electrode are mounted on opposed sides of the substrate for exposing the second electrode to a reference oxygen mixture.

5. A solid state gas sensor according to any one of claims 1–3, where the sensor is an oxidizable gas sensor and the composite equilibrium electrode and second electrode are mounted on the same side of the substrate for exposure to a gas mixture containing oxidizable gases.

* * * * *